(12) United States Patent
Baikoff

(10) Patent No.: US 6,682,560 B1
(45) Date of Patent: Jan. 27, 2004

(54) ELEMENT CORRECTING PRESBYOPIA

(76) Inventor: Georges Baikoff, 317, Corniche Kennedy, Marseilles (FR), F-13007

( * ) Notice: Subject to any disclaimer, the term of this patent is extended or adjusted under 35 U.S.C. 154(b) by 0 days.

(21) Appl. No.: 10/129,457
(22) PCT Filed: Jan. 17, 2002
(86) PCT No.: PCT/FR02/00179
§ 371 (c)(1), (2), (4) Date: Jul. 12, 2002
(87) PCT Pub. No.: WO02/056801
PCT Pub. Date: Jul. 25, 2002

(30) Foreign Application Priority Data

Jan. 19, 2001 (FR) .............................. 01 00703

(51) Int. Cl.[7] .................................................. A61F 2/14
(52) U.S. Cl. ....................................................... 623/4.1
(58) Field of Search ................................ 623/4.1, 6.64, 623/905

(56) References Cited

U.S. PATENT DOCUMENTS

| | | | | |
|---|---|---|---|---|
| 5,489,299 A | * | 2/1996 | Schachar ..................... 623/4.1 |
| 6,007,578 A | * | 12/1999 | Schachar ................... 623/11.11 |
| 6,102,946 A | * | 8/2000 | Nigam ........................ 623/5.15 |
| 6,358,279 B1 | * | 3/2002 | Tahi et al. ..................... 623/4.1 |
| 6,494,910 B1 | * | 12/2002 | Ganem et al. ................. 623/4.1 |
| 6,511,508 B1 | * | 1/2003 | Shahinpoor et al. .......... 623/4.1 |
| 6,579,316 B2 | * | 6/2003 | Schachar ..................... 623/4.1 |

FOREIGN PATENT DOCUMENTS

| | | | |
|---|---|---|---|
| FR | 2784287 | 4/2000 | |
| FR | 2787991 | 7/2000 | |
| WO | WO 00/74600 A1 | * 12/2000 | ................... 623/4.1 |

OTHER PUBLICATIONS pub no. US 2002/0035397 A1 Baikoff.*

* cited by examiner

Primary Examiner—David H. Willse
Assistant Examiner—Suzette J. Jackson
(74) Attorney, Agent, or Firm—Young & Thompson

(57) ABSTRACT

The corrective element (3) is adapted to be implanted in an eye in line with the ciliary body and is shaped, to exert on the ciliary body a centripetal force (F1) directed perpendicularly to the optical axis (2) of the eye.

19 Claims, 1 Drawing Sheet

ELEMENT CORRECTING PRESBYOPIA

The present invention relates generally to the correction of vision by insertion of a corrective element into the eye, and more precisely the correction of presbyopia.

It will be recalled that, as shown in FIG. 1, the lens Cr enclosed in the lens sac S is suspended from the ciliary body Cc by means of the zonule Z. This ciliary body Cc lines the internal surface of the sclera about a ring located on the average at a latitude distant by 2 to 3 mm from the limbus, measured along the optical axis.

Presbyopia is a loss or reduction of the accommodating power of the eye which takes place when the person ages.

According to a theory of about a hundred years ago, Von Helmholtz explained the physiology of the accommodation of near vision by a relaxation of the zonule tension exerted on the lens during contraction of the ciliary body. This relaxation of tension gives rise to the lens taking a more globular form having smaller radii of curvature and hence more convergent as to the focal point. At the same time, the lens move forward in an antero-posterior plane.

Schachar proposed beginning in 1992, particularly in his U.S. Pat. Nos. 5,354,331, 5,465,737, 5,489,299 and 6,007,578, a theory contrary to that of Von Helmholtz, according to which the accommodation was due to a tensile force exerted on the lens when the ciliary body relaxes, such a force tensioning the zonule ligament which creates a flattening of the periphery of the lens and a convex projection of the center of the latter.

Moreover, according to Schachar, the diameter of the lens increases in the course of aging and the distance separating the periphery of the lens from the ciliary body diminishes bit by bit, which leads to a relaxation of the zonule. As a result, the centrifugal effort exerted by the ciliary body on the periphery of the lens is no longer sufficiently great to ensure the accommodation.

Schachar proposed in the patents mentioned above, different methods permitting improving the accommodation power of an eye, consisting for example in surgically reducing the length of the zonules or the diameter of the lens, or preventing enlargement of the lens.

Another method of treatment proposed by Schachar has been very widely used. It consists in treating presbyopia by positioning a truncated conical ring about the scleral ring to create a sort of external suspension, so as to enlarge the diameter of the ciliary body and hence to restretch the zonule.

Such an intervention being fairly important, it has been proposed subsequently to position on the sclera arcuate scleral expansion segments, of a radius of curvature less than the radius of curvature of the sclera. These segments pass through passages encised in the surface of the sclera concentrically to the limbus, in line with the ciliary body, and bear with their ends on the external surface of the sclera.

In FR 98 12834 of the applicant, such segments have ends of spatulate form so as not to risk perforating the sclera at the points of bearing of the segment on the sclera and preventing turning of said segments.

It has been noted that the operations carried out since 1992 by following the Schachar theory have sometimes succeeded and permitted giving the patient good vision, but sometimes not, the accommodation not being really better after the intervention.

Moreover, in certain patients, the segments have been expelled from the sclera, after pulling out of the passages in which they were positioned.

As a result, the Schachar theory is not able to solve the problem of the treatment of presbyopia.

By analyzing the results of procedures practiced by specialists, the applicant as arrived at the conclusion that the Schachar theory was inexact even though its practice permitted in certain cases obtaining the desired result.

The applicant concluded that the correction of presbyopia observed in certain patients after implantation of a truncated conical ring or arcuate segments on the sclera would not do as Schachar thought, to an effect of traction exerted on the zonule and hence on the lens, but to an induced result obtained during the procedure without the operator seeking it.

The applicant has taken account of the fact that the eyeball has a flexible but inextensible surface and has concluded that it is not possible to increase the circumference of the scleral ring by exerting centrifugal tension at certain points on the sclera.

By examining in greater detail the procedures carried out according to the Schachar method, the applicant has determined that by exerting a centrifugal tension at certain points, the emplacement of segments of scleral expansion would exert as a reaction a centripetal pressure in line with their points of bearing on the sclera.

The applicant thus explains the observed effect with certain rings or scleral expansion segments, not by the traction that they exert on the zonule at certain points, but by the pressure that they exert on the latter at other points. When the pressure is exerted in line with the ciliary body, it artificially compensates the defect of contraction of said ciliary body and helps the eye in its accommodation work as was described by Von Helmholtz.

These observations led the applicant to provide by the present invention a corrective element permitting correcting presbyopia reproducibly and not at random, as in the procedures proposed for about the last ten years.

To this end, the invention relates to a corrective element permitting correcting presbyopia, adapted to be implanted in the eye in line with the ciliary body, characterized in that it is shaped to exert on said ciliary body a centripetal force directed perpendicularly to the optical axis.

This element is noteworthy in that it has, in cross-section, an external wall adapted to be disposed parallel to the surface of the sclera and an internal wall adapted to be disposed parallel to the optical axis of the eye.

The sclera being inextensible, such an element acts by bearing on the portion of the sclera which it covers to press the ciliary body in the direction of the optical axis of the eye and to form indentations in said ciliary body. As a result, centripetal forces on said ciliary body artificially compensate the loss of contraction of the latter and thus re-establish its action necessary for accommodation, which is to say the zonular relaxation.

The increase of the contractive force of the ciliary body with a decrease of the diameter of the ciliary ring by elements forming indentations in the ciliary body, permits relaxing the zonule and letting the lens profit from its residual flexibility to become more globular.

The corrective element according to the invention is all the more remarkable in that:
  it is constituted by an arcuate segment whose radius of curvature is such that after its emplacement in the eye, said segment will be centered on the optical axis of said eye,
  a rear wall connects the rear elongated ends to each other of said external and internal walls,
  a rounded portion connects the concurrent front ends of said external and internal walls,
  the angle comprised between the external wall and the internal wall is of the order of 45°, the rear wall is rounded, the rear wall is constituted by a portion of a torus.

The invention will be better understood from the description which follows given by way of non-limiting example and with reference to the accompanying drawings, in which.

Figure 1:
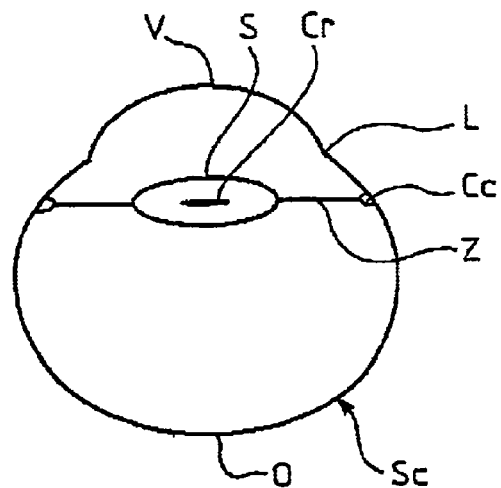
FIG. 1 is a schematic view in cross-section of an eye.
Figure 2:
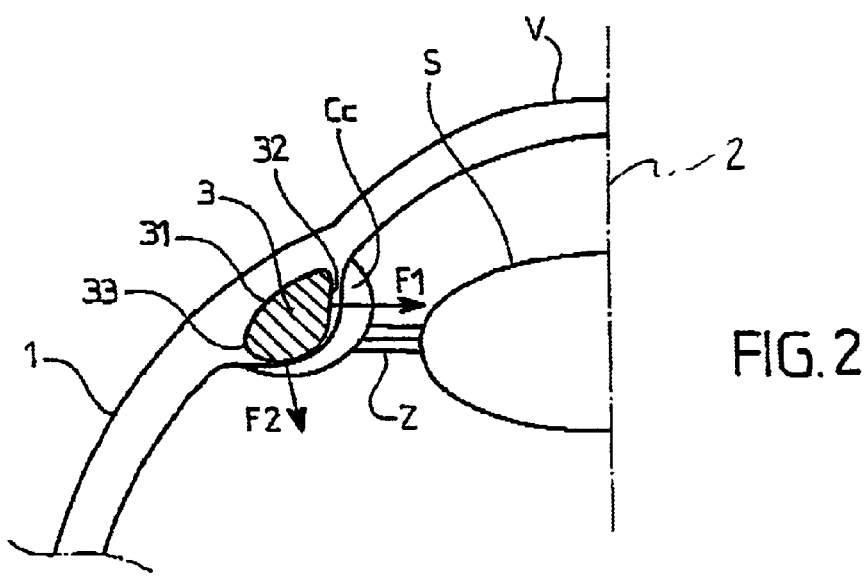
FIG. 2 is a fragmentary cross-sectional view of an eye in which is implanted a corrective element according to the invention.

In FIG. 2, there is schematically shown at 1 the surface of the sclera in line with the ciliary body and at 2 the optical axis of the eye.

The terms front and rear are defined relative to the eye.

Figure 3:
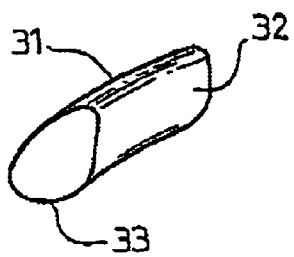
FIG. 3 is a perspective view of a corrective element according to the invention.

FIGS. 2 and 3 show an element 3 according to one preferred embodiment of the invention. This element is constituted by an arcuate segment whose radius of curvature is such that it will be centered on the optical axis 2 of the eye when it is in place, and hence such that said segment will be parallel to the scleral ring at the level of the insertion of the ciliary muscle. Said arcuate segment has for example a length of the order of 4 to 5 millimeters and a radius of curvature of the order of 7 millimeters.

As seen in cross-section, the element 3 overall has the shape of a triangle. It comprises an external wall 31 adapted to be disposed parallel to the surface 1 of the sclera, an internal wall 32 adapted to be disposed parallel to the optical axis 2 of the eye.

Given the geometry of the eye, this external wall 31 and internal wall 32 of the element 3 define between them an angle of about 45°.

Said external wall 31 and internal wall 32 have concurrent ends toward the front of the element 3 and spaced from each other rearwardly.

A rear wall 33 connects the rear spaced ends of the external wall 31 and internal wall 32 and a rounded portion connects the front concurrent ends of the two walls.

In a manner known per se, the sclera is a semi-rigid and inextensible body whilst the ciliary body is a soft tissue. A foreign body introduced between the sclera and the ciliary body thus cannot deform the sclera but gives rise to a deformation of the ciliary body. As a result, when it is emplaced in the eye, in line with the ciliary body, the element 3 bears with its external wall 31 on the inextensible portion of the sclera which covers it to exert on the ciliary body Cc a centripetal force F1 oriented perpendicularly to the internal wall 32, hence perpendicularly to the optical axis 2, and directed toward said optical axis 2. Such a force acts directly on the ciliary body Cc and exerts on the latter a pressure which presses it back in the direction of the optical axis 2 of the eye, which artificially creates a displacement of the latter similar to that which takes place during contraction of said ciliary body. This displacement has the effect of relaxing the zonule Z, along the axis of this latter. This effect compensates the loss of contraction power of the ciliary body and permits the lens to take a more globular shape having smaller radii of curvature.

The front end of the element 3 is preferably rounded so as to avoid harming the tissues of the eye.

The rear wall 33 can be more or less rounded.

Preferably, said rear wall 33 is so arranged as to give to the cross-section of the corrective element 3 a shape similar to a drop, to this end it can be constituted by a toric portion. Such a construction permits further improving the correction arising from the corrective element 3 by supplying a pressure force F2 exerted on the ciliary body Cc by the rear wall 33.

The force F2 is oriented toward the center and toward the rear of the eye, and ensures a compression of the vitreous humor and induces a pressure, and hence a movement, of the lens forwardly similar to that described by Von Helmholtz.

The corrective element 3 according to the invention is disposed at the deep surface of the scleral plane to take best advantage of the forces due to the inextensibility of the sclera and near the surface of the soft body constituted by the ciliary body, through insertions of small dimensions provided in the sclera, or between the sclera and the ciliary body as shown in the drawing.

So as to obtain a maximum effect, the emplacement of the element according to the invention must be carried out by making an incision in the sclera to a depth of at least 600 microns and providing at this depth a blind tunnel extending parallel to the surface of the sclera. Echography can be used before the operation to verify the thickness of the sclera so as not to risk injuring the ciliary body. After insertion of the corrective element, the incision is sutured so that the element remains positioned deep in the sclera.

To treat presbyopia, several elements are distributed in the eye, about the ciliary body, so as to constitute several pressure zones distributed about the lens and to induce in the latter effects similar to that which it undergoes during contraction of a young ciliary body. There will be positioned for example 3 to 8 segments according to the invention in the eye of the patient, preferably 4 segments disposed at 90° from each other.

The corrective element 3 is preferably provided so as to have in cross-section a length parallel to the optical axis such that it will bear against the ciliary body even it is not perfectly well positioned in line with the latter. To this end, the length of the internal wall 32 is for example of the order of 0.5 to 0.7 millimeter.

The length of the external wall 31 is for example of the order of 0.7 to 1 millimeter, and the thickness of the segment 3, defined perpendicular to said internal wall 32, is for example of the order of 0.5 to 0.7 millimeter.

According to an alternative embodiment not shown in the drawing, the corrective element 3 according to the invention is constituted by a cylindrical ring disposed within the sclera, about the ciliary body.

According to still another embodiment not shown in the drawing, the corrective element is not of uniform cross-section over all its length. It can have regions with a triangular cross-section acting on the ciliary body and regions with a smaller cross-section that have no or little action on the ciliary body. Such an embodiment permits creating a large number of points of bearing on the ciliary body so as better to distribute the forces exerted on the latter.

What is claimed is:

1. Element for correcting presbyopia, adapted to be implanted in an eye in line with the ciliary body, characterized in that it is shaped to exert on said ciliary body a centripetal force (F1) directed perpendicularly to the optical axis (2) of the eye.

2. Corrective element according to claim 1, characterized in that it has in its cross-section an external wall (31) adapted to be disposed parallel to the surface of the sclera (1) and an internal wall (32) adapted to be disposed parallel to the optical axis (2) of the eye.

3. Corrective element according to claim 1, characterized in that it is constituted by an arcuate segment (3) whose radius of curvature is such that after its emplacement in the eye, said segment (3) will be centered on the optical axis of said eye.

4. Corrective element according to claim 2, characterized in that a rear wall (33) connects rear ends spaced from each other of said external wall (31) and internal wall (32).

5. Element according to claim 2, characterized in that a rounded portion connects the front concurrent ends of said external wall (31) and internal wall (32).

6. Corrective element according to claim 2, characterized in that the angle between the external wall (31) and the internal wall (32) is of the order of 45°.

7. Corrective element according to claim 4, characterized in that the rear wall (33) is rounded.

8. Corrective element according to claim 4, characterized in that the rear wall (33) is constituted by a portion of a torus.

9. A method for correcting presbyopia, comprising making at least one incision into the sclera of a patient in the vicinity of the ciliary body, thereby to form a tunnel, and implanting into said tunnel an element for correcting presbyopia, said element having a shape and an orientation within said tunnel exerting a centripetal force (F1) on said ciliary body directed perpendicularly to the optical axis (2) of the eye.

10. The method according to claim 9, wherein the incision is made in the sclera to a depth of at least about 600 microns, and wherein said tunnel is a blind tunnel extending parallel to the surface of the sclera.

11. The method according to claim 9, further comprising performing echography prior to making the incision, to ascertain the thickness of the sclera.

12. The method according to claim 9, further comprising suturing the incision after implantation of said element, thereby to retain said element position within said is tunnel in the sclera.

13. The method according to claim 9, wherein said element has in its cross-section an external wall (31) adapted to be disposed parallel to the surface of the sclera (1) and an internal wall (32) adapted to be disposed parallel to the optical axis (2) of the eye.

14. The method according to claim 9, wherein said element is constituted by an arcuate segment (3) whose radius of curvature is such that after its emplacement in the eye, said segment (3) will be centered on the optical axis of said eye.

15. The method according to claim 13, wherein said element comprises a rear wall (33) that connects said rear ends spaced from each other of said external wall (31) and internal wall (32).

16. The method according to claim 13, wherein said element comprises a rounded portion that connects the front concurrent ends of said external wall (31) and internal wall (32).

17. The method according to claim 13, wherein the angle between the external wall (31) and the internal wall (32) is about 45°.

18. The method according to claim 15, characterized in that the rear wall (33) is rounded.

19. The method according to claim 15, characterized in that the rear wall (33) is constituted by a portion of a torus.

* * * * *

(12) EX PARTE REEXAMINATION CERTIFICATE (6099th)
United States Patent
Baikoff

(10) Number: US 6,682,560 C1
(45) Certificate Issued: Jan. 15, 2008

(54) ELEMENT CORRECTING PRESBYOPIA

(75) Inventor: Georges Baikoff, Marseilles (FR)

(73) Assignee: Opthalmic Lenders, LLC, Dallas, TX (US)

Reexamination Request:
No. 90/008,188, Aug. 25, 2006

Reexamination Certificate for:
Patent No.: 6,682,560
Issued: Jan. 27, 2004
Appl. No.: 10/129,457
Filed: Jul. 12, 2002

(22) PCT Filed: Jan. 17, 2002

(86) PCT No.: PCT/FR02/00179

§ 371 (c)(1),
(2), (4) Date: Jul. 12, 2002

(87) PCT Pub. No.: WO02/056801

PCT Pub. Date: Jul. 25, 2002

(30) Foreign Application Priority Data

Jan. 19, 2001 (FR) .............................. 01 00703

(51) Int. Cl.
*A61F 2/14* (2006.01)

(52) U.S. Cl. ...................................... 623/4.1
(58) Field of Classification Search ............... None
See application file for complete search history.

(56) References Cited

U.S. PATENT DOCUMENTS

| 4,564,018 A | 1/1986 | Hutchison et al. | 128/660 |
| 6,007,578 A | 12/1999 | Schachar | 623/4 |
| 6,280,468 B1 | 8/2001 | Schachar | 623/4.1 |
| 6,712,847 B2 | 3/2004 | Baikoff et al. | 623/4.1 |

*Primary Examiner*—Jeffrey R. Jastrzab

(57) ABSTRACT

The corrective element (3) is adapted to be implanted in an eye in line with the ciliary body and is shaped, to exert on the ciliary body a centripetal force (F1) directed perpendicularly to the optical axis (2) of the eye.

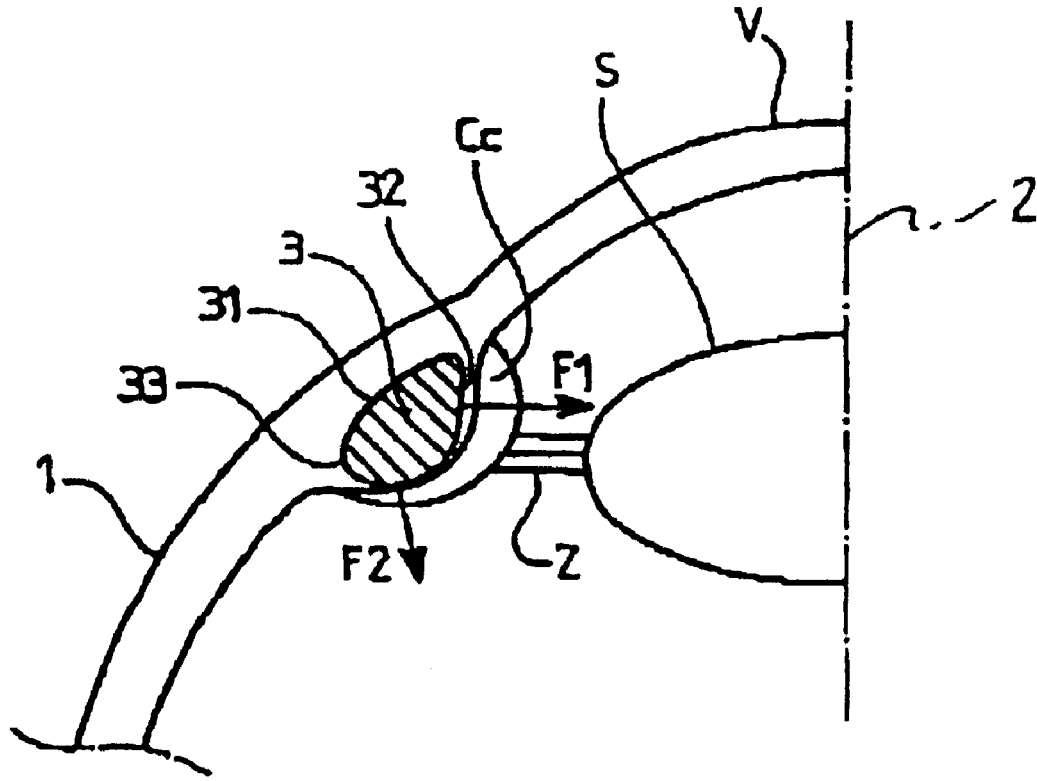

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–19 is confirmed.

New claims 20 and 21 are added and determined to be patentable.

*20. The method according to claim 9, wherein the corrective element is implanted so as to form an indentation in the ciliary body.*

*21. The element according to claim 1, wherein said body, when implanted in the sclera of a patient, forms an indentation in the ciliary body.*

\* \* \* \* \*